United States Patent [19]

Mee

[11] 4,197,080

[45] Apr. 8, 1980

[54] RADIATION-CLEAVABLE NONDIFFUSIBLE COMPOUNDS AND PHOTOGRAPHIC ELEMENTS AND PROCESSES EMPLOYING THEM

[75] Inventor: John D. Mee, Rochester, N.Y.

[73] Assignee: Eastman Kodak Company, Rochester, N.Y.

[21] Appl. No.: 12,171

[22] Filed: Feb. 14, 1979

[51] Int. Cl.$^2$ .................. G03C 5/54; G03C 1/40; G03C 1/72

[52] U.S. Cl. .................... 430/211; 430/235; 430/339

[58] Field of Search .................. 96/29 D, 89, 77, 9

[56] References Cited

U.S. PATENT DOCUMENTS

| Re. 28,225 | 11/1974 | Heseltine et al. | 96/89 |
|---|---|---|---|
| 2,688,541 | 9/1954 | Ganguin et al. | 96/9 |
| 2,885,288 | 5/1959 | Beswick et al. | 96/9 |
| 3,227,550 | 1/1966 | Whitemore et al. | 96/29 D |
| 3,446,619 | 5/1969 | Gilman et al. | 96/89 |
| 3,615,432 | 10/1971 | Jenkins et al. | 96/89 |
| 3,619,194 | 11/1971 | Mitchell | 96/89 |

*Primary Examiner*—Richard L. Schilling
*Attorney, Agent, or Firm*—Joshua G. Levitt

[57] ABSTRACT

Radiation-cleavable nondiffusible compounds for providing a transfer dye image are comprised of a spectral sensitizing dye moiety and a diffusible image dye moiety joined to a linkage in the spectral sensitizing dye moiety which is cleaved upon absorption of radiation by the spectal sensitizing dye moiety, thereby releasing the diffusible dye. Such compounds are useful in radiation-sensitive elements and processes.

12 Claims, No Drawings

RADIATION-CLEAVABLE NONDIFFUSIBLE COMPOUNDS AND PHOTOGRAPHIC ELEMENTS AND PROCESSES EMPLOYING THEM

This invention relates to radiation-cleavable nondiffusible compounds, to radiation-sensitive compositions and elements containing them and to processes of producing images with such compounds, compositions and elements.

Numerous materials are known which can be used to prepare dye images by exposure to radiation. Among these are materials in which a dye is destroyed by imagewise exposure to radiation, leaving in the unexposed areas an imagewise distribution of dye. A particularly useful class of such materials is described in Heseltine et al U.S. Pat. No. 3,615,432 issued Oct. 26, 1971 (U.S. Pat. No. 28,255, Nov. 5, 1974). This patent describes a class of spectral sensitizing dyes which fragment upon exposure to radiation, resulting in bleaching of the dye. Included among the various uses described in the patent for these dyes, and their fragmentation products, is the preparation of dye images formed by the dye remaining in the unexposed areas. (See columns 24 through 28). While these materials result in the preparation of useful images from simple elements using uncomplicated procedures, the images are transitory, unless special processing steps are performed, since the dye forming the image remains sensitive to radiation.

I have found novel nondiffusible compounds based on sensitizing dyes of the type described in the aforementioned Heseltine et al U.S. Pat. No. 3,615,432 which provide permanent dye images.

The nondiffusible compounds of my invention consist of a spectral sensitizing dye moiety and a diffusible image dye moiety joined to a linkage in the spectral sensitizing dye moiety which is cleaved upon absorption of radiation by the spectral sensitizing dye moiety, thereby releasing a diffusible dye. These compounds can be incorporated in a radiation-sensitive element as the sole radiation-sensitive component and yield permanent images by imagewise exposing the element to radiation and transferring the released dye to a separate layer where it will form a permanent image.

The compounds of this invention provide a number of advantages over prior art compounds and elements. They permit the preparation of images using simple materials, and uncomplicated processing steps. They avoid the need for a separate light sensitive component, such as silver halide, and thereby avoid the need for separate layers, such as filter layers, often associated with materials containing such light sensitive components. They permit light sensitive components sensitive to different regions of the spectrum to be incorporated in a single layer or in plural layers arranged in any order desired. Since numerous spectral sensitizing dyes are available which absorb radiation over the entire electromagnetic spectrum, compounds sensitive to particular regions of the spectrum can be prepared using a wide variety of available materials. Similarly, since numerous photographic image dyes are known in a wide variety of colors and hues, numerous materials are available to provide images in a variety of colors and hues. Having one moiety which is sensitive to radiation and a second separate moiety which provides the image enables the two moieties to be selected so as to take maximum advantage of individual properties of each, and permits special effects to be obtained if desired.

Suitable sensitizing dye moieties are preferably chosen from among cyanine and merocyanine dyes containing a pyridine or quinoline ring. In a preferred embodiment the image dye moiety is joined to the nitrogen atom in the pyridine or quinoline ring of the spectral sensitizing dye moiety through an alkoxy linkage. Particularly suitable sensitizing dye moieties are those dyes described in the above referenced U.S. Pat. No. 3,615,432.

The image dye moiety can be selected from any of the preformed or shifted dyes used to form a photographic image. Dyes of this type are well known in the photographic art and include dyes such as azo dyes including metallizable azo dyes and metallized azo dyes, azomethine (imine) dyes, indophenol dyes, anthraquinone dyes, alizarin dyes, quinoline dyes, phthalocyanine dyes and the like. The shifted dyes include those compounds wherein the light-absorption characteristics are shifted hypsochromically or bathochromically when subjected to a different environment such as a change in pH, reaction with a material to form a complex such as with a metal ion, or removal of a group such as a hydrolyzable acyl group connected to an atom of the chromophore. The dye can contain a chelating moiety and upon release can diffuse to an image-receiving layer containing metal ions to form a metal-complexed dye. Particularly suitable dyes are the phenylazonaphthyl dyes of U.S. Pat. Nos. 3,929,760, 3,931,144, 3,932,380, 3,932,381, 3,942,987, 3,854,476, 4,001,204 and 4,013,635, the phenylazopyrazoline dyes of U.S. Pat. No. 4,013,633, the arylazopyrazolotriazole and arylazopyridinol dyes of Baigrie et al U.S. patent application Ser. No. 822,188 filed Aug. 5, 1977; the arylazo dyes of Landholm et al U.S. patent application Ser. No. 850,179 filed Nov. 10, 1977 and Kilminster U.S. patent application Ser. No. 870,314 filed Jan. 18, 1978; the heterocyclylazonaphthol dyes of Chapman U.S. patent application Ser. No. 832,309 filed Sept. 12, 1977; the pyridylazopyrazole and pyrimidylazopyrazole dyes of Green U.S. patent application Ser. No. 832,310 filed Sept. 12, 1977; the pyridylazonaphthol dyes of Anderson et al U.S. patent application Ser. No. 832,499 filed Sept. 12, 1977; the arylazopyridinol dyes of Chapman U.S. patent application Ser. No. 822,189 filed Aug. 5, 1977; the arylazoisoquinolinol dyes of Chapman et al U.S. patent application Ser. No. 884,469 filed Mar. 7, 1978 and the arylazovinylol dyes of Chapman et al U.S. patent application Ser. No. 892,561 filed Apr. 3, 1978.

The compounds of this invention are rendered nondiffusible by virtue of the bulk obtained by attaching the two moieties to one another. However, they can contain, particularly in the sensitizing dye moiety, groups which further enhance nondiffusibility. The sensitizing dye moiety is preferably nondiffusible after release of the image dye moiety therefrom. This eliminates or reduces stain attributable to colored fragmentation or recombination products of the sensitizing dye which otherwise may migrate to the receiving layer. If, however, the sensitizing dye is one whose fragments are not colored and do not recombine to become colored, nondiffusibility of the sensitizing dye moiety is not required. The image dye is chosen so as to be diffusible under processing conditions. It can contain substituents, such as acid groups, which contribute to its diffusibility.

Although for certain applications and effects the image dye can be chosen to absorb in one region of the electromagnetic spectrum and the sensitizing dye moiety be chosen to absorb in a different region of the spectrum, it is preferred that both the sensitizing dye moiety and the image dye moiety absorb in the same region of the electromagnetic spectrum. Thus, a sensitizing dye which absorbs in the blue region of the spectrum (and is colored yellow) would have associated with it an image dye moiety which is yellow, or a precursor thereof which becomes yellow under processing conditions, (and absorbs radiation in the blue region of the spectrum). Similarly, a sensitizing dye moiety which absorbs in the green region of the spectrum would have associated with it a magenta image dye or image dye precursor, and a sensitizing dye moiety which absorbs in the red region of the spectrum would have associated with it a cyan image dye or image dye precursor. Sensitizing dyes which respond to forms of radiant energy other than visible light, or to other forms of energy would have associated an image dye of an absorption appropriate for the desired image.

The radiation sensitive elements of this invention can be relatively simple. They can comprise a support bearing a single layer of one or more nondiffusible compounds of the invention in a suitable binder. The elements can be designed to provide single color or multicolor images. With elements designed to provide multicolor images, the selective absorption of the sensitizing dye moiety permits incorporating dyes sensitive to different regions of the spectrum in a single layer in a uniform or random array. However, compounds sensitive to different regions of the spectrum can be coated in separate layers and these layers arranged in any order desired.

The receiving layer to which the dye is transferred to form a viewable image can simply be a separate sheet of absorbant paper. It is preferably, however, a receiving layer of the type employed in color diffusion transfer processes and comprises a support bearing a layer of a mordant for the image dye. The receiving layer can be on a separate support from the radiation-sensitive element and be brought into contact with the element subsequent to exposure, or it can be integral with the radiation-sensitive element. In the latter case, there would be interposed between the radiation sensitive layer or layers and the receiving layer an opaque layer which is permeable to the image dye and which provides a background against which the image is viewed. Additionally, in the case of an integral receiving layer means are provided, subsequent to imagewise exposure, to block further exposure of the nondiffusible compound.

Images can be prepared with the elements of this invention by exposing the element to radiation and then transferring diffusible dye to a receiving layer.

Elements of this invention are sensitive to various forms of radiant energy. These include electromagnetic radiation such as ultraviolet radiation, visible radiation, infrared radiation, X-radiation; electron beams; laser beams; thermal radiation; heat; and the like. With appropriate compounds and elements of this invention various of these forms of energy can be advantageously used.

After exposure, an image can be formed by transferring the released dye to a suitable receiving layer. If the element does not incorporate the receiving layer, one can be brought into contact with the element after exposure. Transfer can occur as a result of the self-diffusivity of the dye or it can be aided by application of heat and/or an appropriate solvent medium. If heat is applied, the temperature should be below that at which those compounds which are heat-sensitive fragment. Due to the nature of the preferred image dyes, preferred solvent media are alkaline in nature and can comprise aqueous alkaline solutions. They can be applied to the element in various ways, such as by dipping the element or the receiver in the solvent or by breaking a pod containing the solvent over the dye-containing layer.

Inasmuch as dye is released in areas of exposure, there is obtained by the processing technique described above an image which is a negative of the original. In order to obtain a positive image, rather than transferring dye immediately after imagewise exposure, the released dye can be allowed to diffuse out of the element, then the element can be uniformly exposed to any of the forms of radiant energy which will effect fragmentation of the remaining nondiffusible compound and transfer of the release dye to form an image can be effected as described above for the formation of a negative image.

Preferred nondiffusible compounds of this invention can be represented by the structural formula:

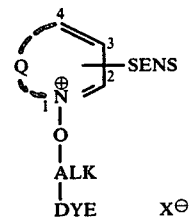

where:

Q represents the atoms to complete a pyridine or quinoline ring;

SENS is attached to the 2 or 4 position of the pyridine or quinoline ring and represents the atoms which, in conjugation with N, complete a spectral sensitizing dye;

ALK represents an alkylene moiety of 1 to 8 carbon atoms;

DYE represents a diffusible photographic dye or dye precursor moiety; and $X^{\ominus}$ represents an anion, if necessary to provide charge neutrality.

In a preferred embodiment, Q represents the atoms to complete a pyridine ring.

In a preferred embodiment SENS represents the atoms to complete, with Q, a cyanine or merocyanine dye and in a particularly preferred embodiment, SENS represents the atoms to complete, with Q, a cyanine dye. Thus, SENS can represent a methine chain of 1 to 7 carbon atoms terminated with a carbocyclic or heterocyclic nucleus of the type used in cyanine and merocyanine dyes.

In a preferred embodiment ALK represents an alkylene moiety of 1 to 4 carbon atoms.

In a preferred embodiment DYE represents an azo dye moiety.

It will be appreciated that in the above structural formula the moiety

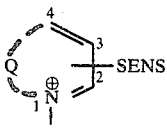

together with the O-ALK linkage is the sensitizing dye moiety discussed previously. Preferred such moieties are described in U.S. Pat. No. 3,615,432 and can be represented by the structures:

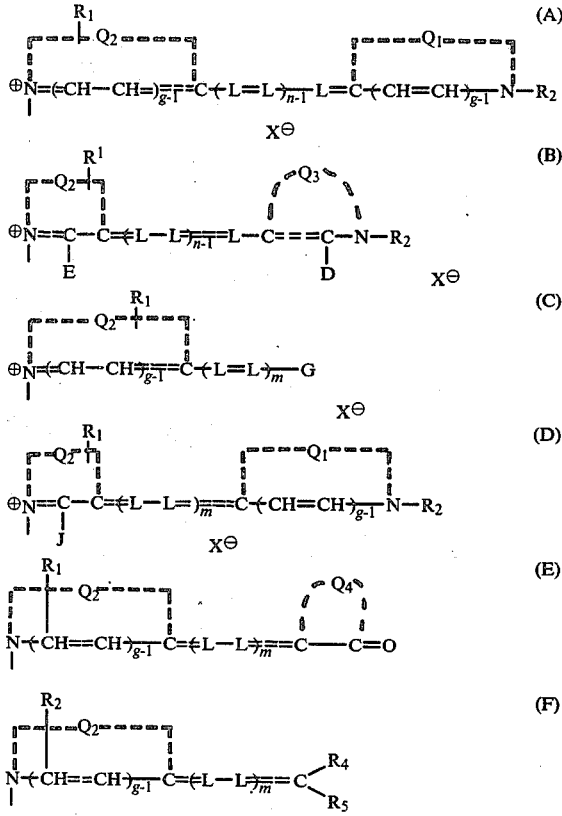

wherein:

$Q_1$ and $Q_3$ each represent the nonmetallic atoms necessary to complete a sensitizing dye nucleus containing 5 or 6 atoms in the heterocyclic ring, which nucleus can contain at least one additional hetero atom such as oxygen, sulfur, selenium or nitrogen, i.e., a nucleus of the type used in cyanine dyes such as the following representative nuclei: a thiazole nucleus, an oxazole nucleus, a selenazole nucleus, a thiazoline nucleus, a pyridine nucleus, a quinoline nucleus, a 3,3-dialkylindolenine nucleus, preferably having a nitro or cyano substituent, an imidazole nucleus, an imidazo [4,5-b]-quinoxaline nucleus, a 3,3-dialkyl-3H-pyrrolo[2,3-b]pyridine nucleus, a thiazolo[4,5-b]-quinoline nucleus; an indolyl nucleus and the like;

$Q_2$ represents the atoms necessary to complete a pyridine nucleus or a quinoline nucleus;

$Q_4$ represents the nonmetallic atoms required to complete a 5 to 6-membered heterocyclic nucleus of the type used in merocyanine dyes, typically containing a hetero atom selected from nitrogen, sulfur, selenium, and oxygen, such as a 2-pyrazolin-5-one nucleus; an oxindole nucleus, a 2,4,6-triketohexahydropyrimidine nucleus, a rhodanine nucleus, a 2(3H)-imidazo-[1,2-a]-pyridone nucleus; a 2-furanone nucleus; a 5,7-dioxo-6,7-dihydro-5-thiazolo[3,2-a]-pyrimidine nucleus; a 2-thio-2,4-oxazolidinedione nucleus; a 2-thio-2,5-thiazolidinedione nucleus; a 2-imino-4-oxazolidinone nucleus; a 2,4-imidazolidinedione nucleus; a 2-thio-2,4-imidazolidinedione nucleus and the like;

L represents a methine linkage having the formula

wherein T is hydrogen, lower alkyl of one to four carbon atoms or aryl such as phenyl, e.g., —CH=, —C(CH$_3$)=, —C(C$_6$H$_5$)=, etc.;

D, E, J, $R_1$ and $R_3$ each represent a hydrogen atom, an alkyl group (preferably a lower alkyl containing from one to four carbon atoms), e.g., methyl, ethyl, propyl, isopropyl, butyl, decyl, dodecyl, etc., or an aryl group, e.g., phenyl, tolyl, naphthyl, methoxyphenyl, chlorophenyl, nitrophenyl, etc.;

$R_2$ represents an alkyl group, including substituted alkyl (preferably a lower alkyl containing from 1 to 4 carbon atoms), e.g. methyl, ethyl, propyl, isopropyl, butyl, hexyl, cyclohexyl, decyl, dodecyl, etc., and substituted alkyl groups (preferably a substituted lower alkyl containing from 1 to 4 carbon atoms), such as a hydroxyalkyl group, a carboxyalkyl group, an alkoxy group, a sulfoalkyl group, a sulfatoalkyl group, an acyloxyalkyl group, an acyloxyalkyl group, an alkoxycarbonyl group, or an aralkyl group, an alkenyl group, or an aryl group;

$R_4$ and $R_5$ each represent a cyano radical, an ester radical such as ethoxy carbonyl, methoxycarbonyl, etc., or an alkylsulfonyl radical such as ethylsulfonyl, methylsulfonyl, etc.;

G represents an anilino radical or an aryl radical, e.g., phenyl, naphthyl, dialkylaminophenyl, tolyl, chlorophenyl, nitrophenyl, anilinovinyl, etc.;

X represents an acid anion, e.g., chloride, bromide, iodide, perchlorate, tetrafluoroborate, sulfamate, thiocyanate, p-toluenesulfonate, methylsulfate, etc.;

n is a positive integer from 1 to 4;
m is a positive integer from 1 to 3; and
g is a positive integer from 1 to 2.

The moiety —O—ALK— in the above structural formula I represents a preferred linking group. Examples of alkylene moieties, represented by ALK, are methylene, ethylene, propylene, isopropylene, butylene, tertiary butylene, pentylene, hexylene, oxtylene, and the like. Particularly preferred are alkylene moieties of 1 to 4 carbon atoms.

Preferred DYE moieties in the above structural formula I are azo, azomethine, indophenol, anthraquinone and phthalocyanine dye moieties. Particularly preferred are azo dye moieties.

The dye moiety can be a preformed dye, which has the color and hue desired for the image, or it can be a shifted dye which has a color and hue different from that desired for the image but which in the processing environment or upon release from the sensitizing dye moiety shifts to the color and hue desired. Preferred dye moieties can be represented by the structure:

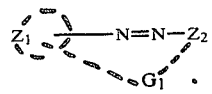

wherein:

$Z_1$ represents the atoms necessary to complete an aromatic, carbocyclic or heterocyclic nucleus containing at least one ring of 5 to 7 atoms (such as phenyl, naphthyl, pyridyl, pyrimidyl, indolyl, pyrazolyl, pyrazolotriazolyl, isoquinolyl and the like);

$Z_2$ represents a nucleus as defined for $Z_1$ or an acyclic unsaturated group such as vinyl, butadienyl, and the like in conjugation with the azo group represented by —N=N—; and $G_1$ represents an auxochromic group of the dye, such as a hydroxy, mercapto or amino group, or a precursor of such a group, in conjugation with the azo group represented by —N=N—.

The groups represented by $Z_1$ and $Z_2$ can be substituted with such groups as alkyl, alkoxy, hydroxy, mercapto, halo, aryl, cyano, nitro, amino, carbonyl, carbamyl, carbonamido, sulfonyl, sulfamyl, sulfonamido, and the like.

The ALK portion of the linking group can be joined to the dye through the auxochromic group $G_1$, or it can be joined to a substituent on $Z_1$ or $Z_2$ such as a carboxy, carbonyl, carbonamido, sulfamyl, or sulfonamido substituent.

The nondiffusible compounds of this invention can be prepared by preparative techniques well known in the art. The image dye moiety can be condensed with a sensitizing dye of the type described in the above referenced U.S. Pat. No. 3,615,432 or it can be condensed with an intermediate for such a sensitizing dye and the nondiffusible compound then formed by further reactions which lead to the sensitizing dye.

The compositions of this invention can be prepared by dispersing the nondiffusible compound in a suitable binder together, if desired, with such addenda as coating aids, hardeners, pH modifiers, buffering agents and the like. Suitable materials for this purpose are described in *Research Disclosure*, December 1971, Item 9232, page 108. *Research Disclosure* is published by Industrial Opportunities Ltd., Homewell, Havant, Hampshire, PO9 1EF, United Kingdom. Gelatin is a preferred binder.

The elements of this invention can be prepared by coating one or more of the above described elements on a support. Suitable coating techniques and supports are described in *Research Disclosure*, December 1971, Item 9232, pages 108 and 109.

The following are preferred nondiffusible compounds of the invention.

Nondiffusible Compounds With Yellow Image Dyes

1.

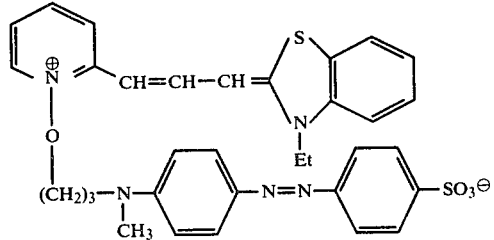

2.

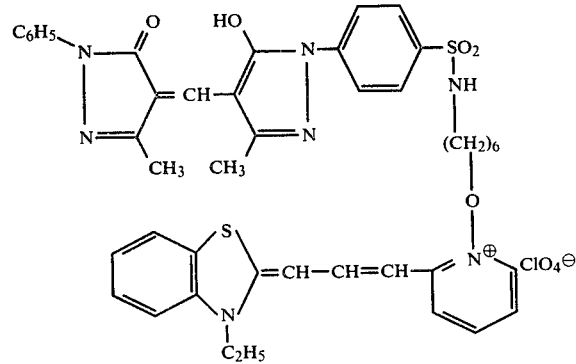

-continued
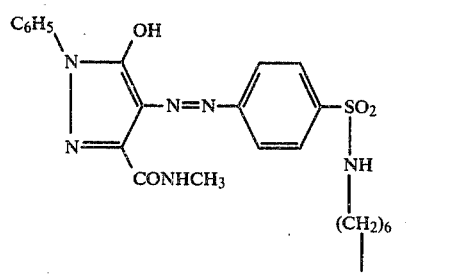
3.
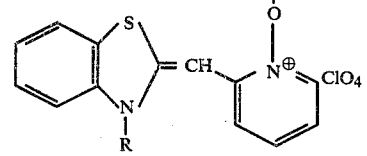
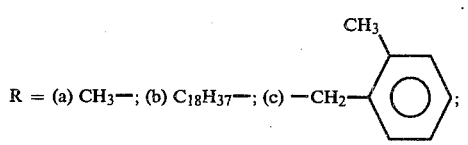
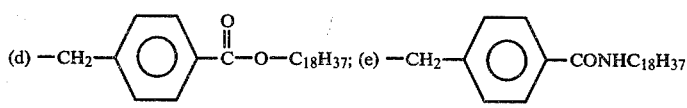
Nondiffusible Compounds With Magenta Image Dyes.
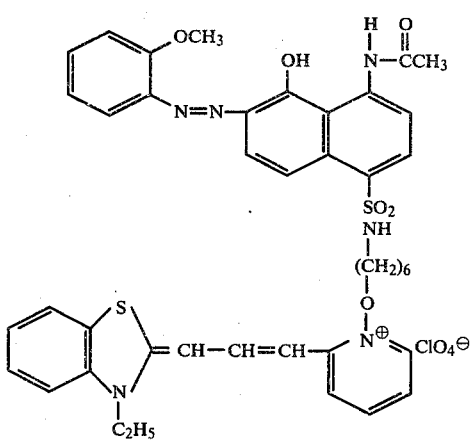
4.
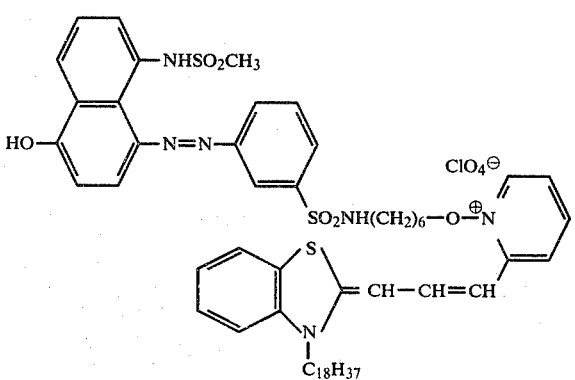
5.

-continued

6.
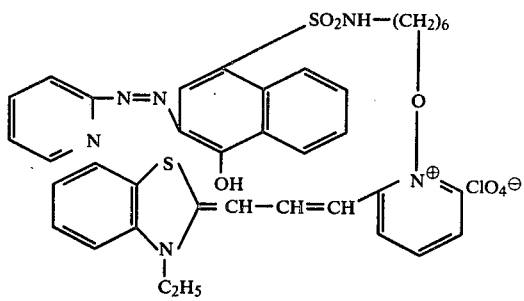

Nondiffusible Compound With A Cyan Image Dye

7.
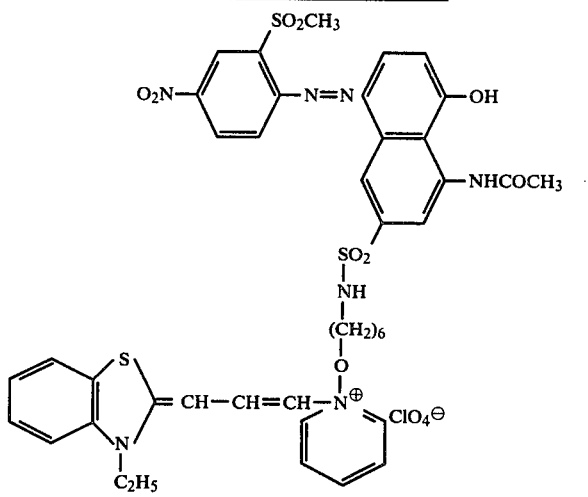

The following examples further illustrate this invention.

EXAMPLE 1

Preparation of Nondiffusible Compound 1

A. Preparation of 1-[3-(N-Methylanilino)propoxy]-2-picolinium perchlorate

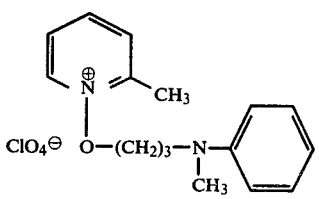

3-(N-Methylanilino)propyl p-toluenesulfonate (21.2 g, 0.0665 mole) and 2-picoline-N-oxide (7.3 g, 0.0665 mole) were heated together on a steam bath for ½ hour. The mixture was allowed to cool, then dissolved in methanol (50 ml). A solution of sodium perchlorate (9.3 g, 0.076 mole) in water (12 ml) was added and the mixture chilled. The solid which separated was collected and washed with a little 90% methanol, then with ether. The yield was 14.3 g (60%), m.p. 111°–113° C.

B. Preparation of Anhydro-1-{3-[4-(4-sulfophenylazo)-N-methylanilino]-propoxy}-2-picolinium hydroxide

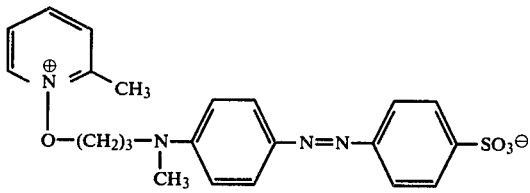

Sulfanilic acid, sodium salt dihydrate (5.8 g, 0.025 mole) was dissolved in water (25 ml), cooled to <15° C., and sodium nitrite (1.75 g, 0.025 mole) added. This solution was added in one lot to a mixture of concentrated hydrochloric acid (5 ml) and ice (30 g). A white solid separated rapidly. This suspension was added, with stirring, to a suspension of 1-[3-(N-methylanilino)-propoxy]-2-picolinium perchlorate from part A (9.0 g, 0.025 mole) in a 1:5 propionic:acetic acid mixture (175 ml) at 0°–5° C. After a further 2 hours' stirring at 0°–5°, the mixture was stirred overnight at room temperature. Solid material was collected and washed with acetic acid, then acetone. Dilution of the reaction mixture to 2.5 l. with acetone yielded more solid which was washed similarly. The solid material was suspended in water and treated with a saturated solution of sodium bicarbonate until no more carbon dioxide was evolved. The solid was collected, washed with water, then acetone. After drying in vacuo, the yield was 3.0 g (27%), no distinct m.p.

C. Preparation of the Nondiffusible Compound Anhydro-3'-ethyl-1-{3-[4-(4-sulfophenylazo)-N-methylanilino]propoxy}2-pyridothiacarbocyanine hydroxide

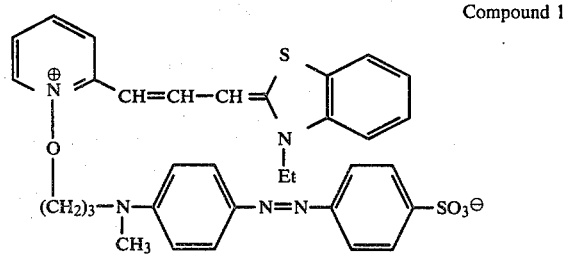

Compound 1

Anhydro-1-{3-[4-(4-sulfophenylazo)N-methylaniline]propoxy}2-picolinium hydroxide from part B (0.66 g, 0.0015 mole), 2-β-acetanilidovinyl-3-ethylbenzothiazolium iodide (1.35 g, 0.0015 mole) and triethylamine (1.5 g) in 50% aqueous pyridine (9 ml) was heated at reflux, with constant stirring, for approximately 30 seconds. The mixture was filtered while hot and the filtrate diluted to 50 ml with methanol. After chilling, the solid was collected and well washed with methanol containing a little triethylamine, then washed with ether. The solid was dried in vacuo at room temperature in the dark. The yield was 0.61 g (65%). No distinct m.p.

EXAMPLE 2

Preparation of Nondiffusible Compound 3d

A. Preparation of Compound 3d.

1-{6-[4-(5-Hydroxy-3-Methylcarbamoyl-1-Phenyl-3(1H)-Pyrazolylazo)benzenesulfonamido]Hexyloxy}-3'-(4-Octadecyloxycarbonylbenzyl)-2-Pyridothiocyanine Perchlorate.

1-{6-[4-(5-Hydroxy-3-methylcarbamoyl-1-phenyl-3(1H)-pyrazolylazo)benzenesulfonamido]hexyloxy}-2-methylpyridinium perchlorate (I-1, 0.69 g) and 2-methylthio-3-(4-octadecyloxy carbonylbenzyl)benzothiazolium perchlorate (I-2, 0.8 g) were dissolved in hot acetonitrile (30 ml), combined with triethylamine (2 ml) and allowed to react at room temperature for 64 hours in the dark. A viscous solid was collected by filtration and washed with ethanol; yield 0.3 g (25%). The compound is light sensitive and must be stored in the dark.

B. Preparation of Intermediate I-1

Step 1

Synthesis of 4-[4-(6-bromohexylsulfamoyl)phenylazo]-5-hydroxy-3-methylcarbamoyl-1-phenyl-1H-pyrazole

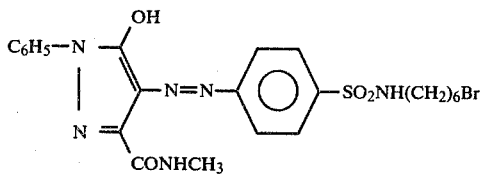

A suspension of 4-(4-chlorosulfonylphenylazo)-5-hydroxy-3-methylcarbamoyl-1-phenyl-1H-pyrazole (12 g) and 6-bromohexylamine hydrobromide (12 g) in 2,6-lutidine (300 ml) and di-isopropylethylamine (3 ml) was allowed to react for 18 hours at room temperature. The reaction mixture was filtered; the filtrate was concentrated to yield an oily material which was washed with hot water to yield the above-identified pyrazole derivative; yield 7.4 g (44%), m.p. 234°–236° C.

Step 2

Synthesis of Intermediate I-1

The pyrazole derivative from Step 1 (5.1 g) and α-picoline-N-oxide (5.1 g) were combined and heated in an oil bath for 70 min/90°–95° C. The mixture was cooled to room temperature dissolved in CH$_3$CN/CHCl$_3$ (1:1, 50 ml) and chromatographed on silica gel. The undesired product was eluted with chloroform, followed by acetonitrile. The product was obtained by eluting with CH$_3$CN/HOAC (8:2). Evaporation of the eluate yielded a solid which was converted to the perchlorate salt by treating with a sodium perchlorate solution; yield 3.4 g (55%), m.p. 165°–7° C.

C. Preparation of Intermediate I-2

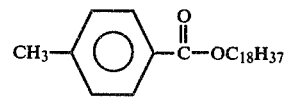

Step 1

Preparation of p-octadecyl toluate

A solution of p-toluoyl chloride (35.7 g), octadecyl alcohol (54 g) and benzene (300 ml) was refluxed for 5 days. Evaporation of the organic solvent provided an oil which was slurried with aqueous sodium bicarbonate to eliminate unreacted acyl chloride, extracted with chloroform, concentrated to an oil once again and washed with acetonitrile and ethanol to produce a white solid; yield 72 g, m.p. 43°–45° C.

Step 2

Preparation of 4-octadecyloxycarbonylbenzyl bromide

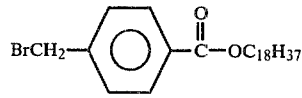

A suspension of p-octadecyl toluate (23.3 g, Step 1), N-bromosuccinimide (10 g) and m-chloroperbenzoic acid (3 g) in carbon tetrachloride was refluxed for 2 hours under a 60 W UV lamp. The reaction mixture was cooled and filtered; the filtrate was treated with aqueous sodium bicarbonate solution. The orange colored organic layer was separated from the aqueous layer and concentrated to an oily residue which was stirred with ethanol to produce a white solid; yield 20 g, m.p. 53°–55° C.

Step 3

Preparation of 3-(4-octadecyloxycarbonylbenzyl)benzothiazoline-2-thione

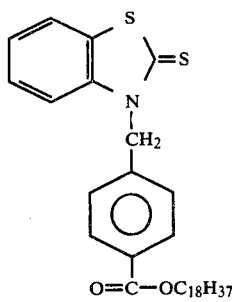

4-Octadecyloxycarbonylbenzyl bromide (4.7 g, Step 2) and 2-methylmercaptobenzothiazole (2.5 g) were heated together for 35 minutes/190°–195° C. The mixture was cooled and triturated with ligroin to produce a solid which was recrystallized from pyridine/methanol to form the product; yield 4.5 g (81%), m.p. 105°–107° C.

Step 4

Synthesis of I-2

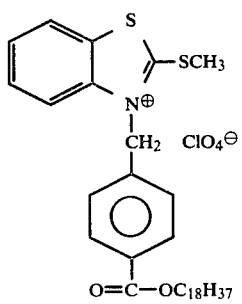

3-(4-Octadecyloxycarbonylbenzyl)benzothiazoline-2-thione (3.5 g, Step 3) and methyl p-toluenesulfonate (2.5 g) were heated together in an oil bath for 1 hour (145°±5° C.). The reaction mixture was cooled to room temperature and combined with ethyl ether (500 ml); the resulting solid (3.6 g) was collected by filtration, dissolved in methanol and converted to the perchlorate salt by adding a solution of methanol (10 ml) and sodium perchlorate (5 g). I-2 was collected by filtration and dried; yield 2.4 g (65%), m.p. 212°–214° C.

EXAMPLE 3

Preparation of Nondiffusible Compound 5

A. Preparation of Compound 5

1-{6-[3-(4-hydroxy-8-methanesulfonamido-1-naphthylazo)phenylsulfonamido]hexyloxy}-3-octadecyl-2-pyridothiocarbocyanine perchlorate.

1-{6-[3-(4-hydroxy-8-methanesulfonamido-1-naphthylazo)phenylsulfonamido]hexyloxy}-2-methylpryidinium perchlorate (I-3, 0.8 g), 2-(2-acetanilidovinyl)-3-octadecylbenzothiazolium perchlorate (I-4, 0.85 g) and triethylamine (2 ml) were combined in hot acetonitrile (20 ml) and reacted for two days at room temperature in the dark. A viscous solid was collected by filtration, stirred with ethyl alcohol (500 ml), isolated again by filtration and dried; yield 0.66 g (53%), m.p. 148°–150° C. The material is light sensitive and must be stored in the dark.

B. Preparation of I-3

Step 1

Synthesis of 4-[3-(6-Bromohexylsulfamoyl)phenylazo]-5-methanesulfonamido-1-naphthol

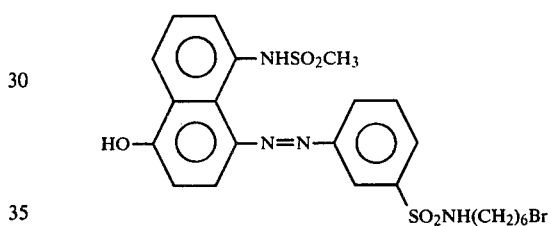

A suspension of 4-[3-chlorosulfonylphenylazo]-1-ethoxycarboxy-5-methanesulfonamidonaphthalene (20.4 g), 6-bromohexylamine hydrobromide (14.4 g), 2,6-lutidine (600 ml) and tetrahydrofuran (30 ml) was reacted for one hour at 50°–55° C. The mixture was cooled and filtered; the filtrate was concentrated to an oil which was dissolved in a minimum amount of acetonitrile and chromatographed on silica gel using acetonitrile as the eluant. The orange colored eluate was concentrated and cooled to obtain the product; yield 7.3 g (32%), m.p. 163°–5° C.

Step 2

Synthesis of I-3

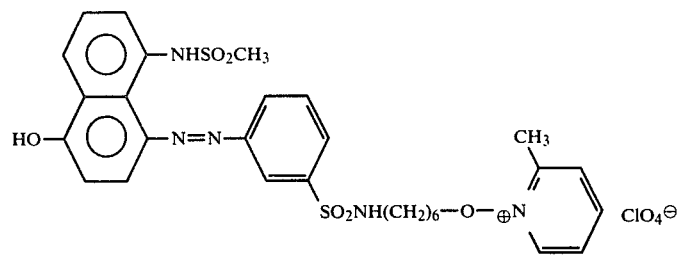

4-[3-(6-Bromohexylsulfamoyl)phenylazo]-5-methanesulfonamido-1-naphthol (Step 1, 2.5 g) and α-picoline-N-oxide (2.5 g) were combined and heated in an oil bath for 1 hour/95° C. The reaction mixture was cooled to room temperature, dissolved in a minimum amount of acetonitrile/chloroform and chromatographed on silica gel. Chloroform was used to remove unreacted starting material followed by acetonitrile to eliminate a by-product. Finally, the product was obtained by eluting with CH₃CN:HOAC (8:2), concentrating in vacuo to obtain a solid, dissolving in acetone/CH₃CN (1:1, 100 ml) and treating the solution with NaClO₄/CH₃CN (5 g/10 ml). The solution was concentrated in vacuo to obtain a solid which was washed with water and dried; yield 1 g (34.5%), m.p. 155°–158° C.

C. Preparation of I-4

Step 1

Synthesis of 2-(2-Anilinovinyl)-3-octadecylbenzothiazolium perchlorate

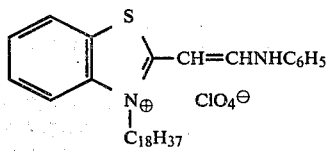

A solution of 2-methyl-3-octadecylbenzothiazolium p-toluenesulfonate (17.2 g) in hot acetonitrile (400 ml) was mixed with a solution of N,N-diphenylformamidine (6.1 g) in hot acetonitrile (75 ml), refluxed for 2 hours, cooled to room temperature and filtered. The filtrate was concentrated in vacuo to approximately 200 ml and cooled to yield a solid (4.7 g). The solid was converted to the perchlorate salt; yield 4.0 g (22%), m.p. 95°–97° C.

Step 2

Synthesis of I-4

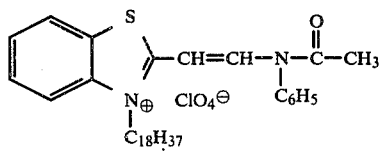

2-(2-Anilinovinyl)-3-octadecylbenzothiazolium perchlorate (Step 1, 3.9 g) was refluxed with acetic anhydride (20 ml) for 5 minutes and then cooled to room temperature to yield 3.4 g of crude product after filtration. The crude material was dissolved in acetone/acetonitrile (300 ml, 1:2) and decolorized with activated charcoal. The filtrate was concentrated to dryness; yield 2.8 g, m.p. 140°–142° C.

EXAMPLE 4

Nondiffusible compound 1 prepared in Example 1 (40 mg) was dissolved in 1.2 molar hydrochloric acid (4 ml) and this solution added, with stirring to a melt of 10% gelatin (8 g), saponin (0.5 ml) and water (6.5 ml). 2.5 molar sodium hydroxide solution was then added to the melt until pH 5.5 was reached, then the melt was coated at a thickness of 0.008 inch on a paper support.

A receiver comprising a paper support coated with a layer containing a basic polymeric mordant was immersed in 0.01 molar sodium hydroxide.

A portion of the element containing the nondiffusible compound was imagewise exposed (3 minutes to a 300 watt tungsten photoflood lamp at 18 inches), and then was pressed in contact with the receiver for 1 minute. A yellow dye image corresponding to the exposed area of the element was obtained on the receiver sheet.

EXAMPLE 5

An element was prepared and exposed as in Example 4, washed with water to remove solubilized dye, and then given an over-all exposure (2 minutes to a 300 watt tungsten photoflood lamp at 18 inches). Dye transfer to a receiver sheet was then carried out as in Example 4. A yellow dye image of the initially unexposed area was obtained on the receiver sheet.

EXAMPLE 6

Nondiffusible compound 5 prepared in Example 3 (60 mg) was dissolved in 1-methyl-2-pyrrolidinone (2 ml) and added to an aqueous solution comprising water (5 ml), saponin (0.5 ml), gelatin (3.2 g) and formaldehyde hardener. The composition was coated on polyethylene terephthalate film support at 0.004 inch. The hardened coating was immersed in aqueous sodium hydroxide (2.5%) and then laminated to a receiver sheet comprising poly(styrene-co-N-vinylbenzyl-N,N,N-trihexylammonium chloride) and gelatin. The sandwich was exposed through the base of the support for 3 minutes using a 300 watt tungsten light located 10 inches from the support. After allowing 3 minutes for transfer the sandwich was separated and the receiver was washed with water. An absorption spectrum showed that approximately 80% of the dye was transferred ($\lambda_{max}$ 565 nm) from the exposed coating.

This invention has been described in detail with particular reference to preferred embodiments thereof, but it will be understood that variations and modifications can be effected within the spirit and scope of the invention.

What is claimed is:

1. A radiation-sensitive element comprising a support bearing a layer of a nondiffusible radiation-cleavable compound consisting of a spectral sensitizing dye moiety containing a pyridine or quinoline nucleus and a diffusible preformed or shifted image dye moiety, the diffusible image dye moiety being joined to the nitrogen atom of the pyridine or quinoline nucleus in the spectral sensitizing dye moiety through an alkoxy linkage which is cleaved upon absorption of radiation by the spectral sensitizing dye moiety, thereby releasing a diffusible dye.

2. An element of claim 1 wherein the spectral sensitizing dye moiety is a cyanine or merocyanine dye moiety.

3. An element of claim 2 wherein the diffusible image dye moiety is an azo, azomethine, indophenol, anthraquinone, alizarin, quinoline or phthalocyanine dye moiety.

4. An element of claim 1, wherein the nondiffusible radiation-cleavable compound has the structure:

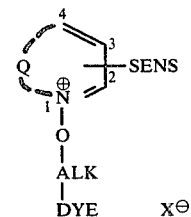

where:

Q represents the atoms to complete a pyridine or quinoline ring;

SENS is attached to the 2 or 4 position of the pyridine or quinoline ring and represents the atoms which, in conjunction with N, complete a spectral sensitizing dye;

ALK represents an alkylene moiety of 1 to 8 carbon atoms;

DYE represents a diffusible preformed or shifted photographic dye moiety; and $X^\ominus$ represents an anion, if necessary to provide charge neutrality.

5. An element of claim 4 wherein SENS represents the atoms which, with Q, complete a cyanine or merocyanine dye.

6. An element of claim 5 wherein DYE represents an azo, azomethine, indophenol, anthraquinone, alizarin, quinoline or phthalocyanine dye moiety.

7. An element of claim 4 wherein

Q represents the atoms necessary to complete a pyridine ring;

SENS represents the atoms necessary to complete, with the pyridine ring, a cyanine dye;

ALK represents an alkylene moiety of 1 to 4 carbon atoms; and

DYE represents an azo dye moiety.

8. A photographic combination comprising an element of claim 1 having associated therewith a receiving layer.

9. A combination of claim 8 wherein the receiving layer is an integral part of the element.

10. An element of claim 1 wherein the nondiffusible radiation-cleavable compound is selected from the group consisting of anhydro-3'-ethyl-1-3-[4-(4-sulfophenylazo)N-methylanilino]propoxy 2-pyridothiacarbocyanine hydroxide; 1-{6-[4-(5-hydroxy-3-methylcarbamoyl-1-phenyl-3(1H)-pyrazolylazo)benzenesulfonamido]-hexyloxy}-3'-[4-octadecyloxycarbonylbenzyl]-2-pyridothiocyanine perchlorate; and 1-{6-[3-(4-hydroxy-8-methanesulfonamido-1-naphthylazo)phenylsulfonamido]-hexyloxy}-3-octadecyl-2-pyridothiocarbocyanine perchlorate.

11. A process of preparing a dye image which comprises exposing to an imagewise pattern of radiation an element of claim 1 to release an imagewise distribution of diffusible dye and transferring the diffusible dye to a receiving layer.

12. A process of preparing a dye image with an element of claim 1 which comprises imagewise exposing the element to radiation to release an imagewise distribution of diffusible dye, removing the imagewise distribution of diffusible dye from the element, uniformly exposing the element to radiation to thereby release a second imagewise distribution of diffusible dye and transferring the second imagewise distribution of diffusible dye to a receiving layer.

* * * * *